United States Patent [19]

Chartrain et al.

[11] Patent Number: 5,605,819
[45] Date of Patent: Feb. 25, 1997

US005605819A

[54] QUANTITATIVE CONVERSION OF INDENE TO (1S,2R) INDENE OXIDE AND (1S,2R)-INDANDIOL BY COMBINATION OF HALOPEROXIDASE BIOCONVERSION AND CHEMICAL STEPS

[75] Inventors: Michel M. Chartrain, Westfield; Neal C. Connors, Fanwood; George M. Garrity, Westfield; Roger C. Olewinski, Jr., Milltown; Thomas R. Verhoeven, Cranford; Jinyou Zhang, Edison, all of N.J.

[73] Assignee: Merck & Co., Inc., Rahway, N.J.

[21] Appl. No.: 445,154

[22] Filed: May 19, 1995

[51] Int. Cl.$^6$ ............................. C12P 17/02; C12P 7/22; C12P 1/02; C12P 5/00
[52] U.S. Cl. ..................... 435/123; 435/156; 435/166; 435/171; 435/192; 435/280; 435/911
[58] Field of Search ...................... 435/123, 166, 435/156, 280, 192, 911, 171

[56] References Cited

U.S. PATENT DOCUMENTS 5,413,999   5/1995   Vacca et al. .
5,420,353   5/1995   Verhoeven et al. .

OTHER PUBLICATIONS

"ATCC Collection of Filamentous Fungi" pp. 139–140 (Curvularia Protuberata) 18th Ed (1991).
American Type Culture Collection Receipt for Curvularia protuberata, MF 5400 –ATCC Designation 74332, Mar. 28, 1995.

*Primary Examiner*—Herbert J. Lilling
*Attorney, Agent, or Firm*—Roy D. Meredith; Jack L. Tribble

[57] ABSTRACT

A process is disclosed that quantitatively bioconverts indene to (1S,2R)-indene oxide and (1S,2R)-indandiol, by the action of fungal haloperoxidase followed by various chemical step(s), e.g., adjusting the pH.

18 Claims, No Drawings

QUANTITATIVE CONVERSION OF INDENE TO (1S,2R) INDENE OXIDE AND (1S,2R)-INDANDIOL BY COMBINATION OF HALOPEROXIDASE BIOCONVERSION AND CHEMICAL STEPS

BACKGROUND OF THE INVENTION

The present application is related to Merck 18996, U.S. Ser. No. 08/059,038, filed May 7, 1993, 18996IA, U.S. Ser. No. 08/235,576, filed Apr. 29, 1994, Merck 19251, Merck 19114 and Merck 19115.

The present invention is concerned with a process for synthesizing intermediates for compounds which inhibit the protease encoded by human immunodeficiency virus (HIV), and in particular certain oligopeptide analogs, such as Compound J in the Examples below. These compounds are of value in the prevention of infection by HIV, the treatment of infection by HIV and the treatment of the resulting acquired immune deficiency syndrome (AIDS). These compounds are also useful for inhibiting renin and other proteases.

The invention described herein concerns the conversion of indene to chiral indan oxide, as illustrated by the following scheme.

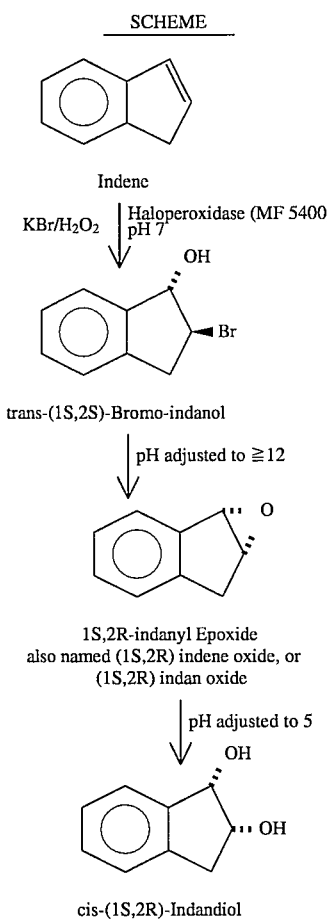

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.,* 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature,* 313,277 (1985)]. Amino acid sequence homology provides evidence that the pol sequence encodes reverse transcriptase, an endonuclease and an HIV protease [Toh, H. et al., *EMBO J.,* 4, 1267 (1985); Power, M. D. et al., *Science,* 231, 1567 (1986); Pearl, L. H. et al., *Nature,* 329, 351 (1987)]. The end product compounds, including certain oligopeptide analogs that can be made from the novel intermediates and processes of this invention, are inhibitors of HIV protease, and are disclosed in EPO 541,168, which published on May 12, 1993. See, for example, Compound J therein, also illustrated in the Examples below.

The present application discloses an improved process to make, in substantial enantiomeric purity, 1(S)-hydroxy-2(R)-hydroxy indan of the structure

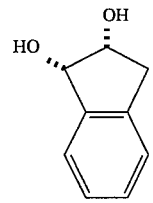

which is a sidechain group of Compound J, which is a potent inhibitor of HIV protease.

Previous attempts at synthesis involve inefficient production of the racemate 1(±)-amino-2(±) hydroxy indan from the racemic indene oxide. Applicants have discovered a fungal preparation that bioconverts indene to predominantly trans-(2S,1S)-bromo-indanol. Further, applicants have found that the adjustment of the pH of the reaction mixture to about 12 quantitatively converts trans-(2S,1S)-bromo-indanol to (1S,2R) indan oxide (85% ee). Prior methods of preparing the same chiral oxide from indene typically gave yields of about 10% or less. Conversion of (1S,2R)-indan oxide to (1S,2R)-indandiol (82% ee) is readily performed.

BRIEF DESCRIPTION OF THE INVENTION

The present invention provides new methods to effect the synthesis of (1S,2R) indan oxide, by bioconversion. Subsequent chemical steps permit formation of (1S,2R)-indandiol, another intermediate. The product compounds are intermediates for compounds useful in the synthesis of inhibitors of HIV protease, renin and other proteases, e.g., Compound J.

DETAILED DESCRIPTION OF THE INVENTION

The present invention is concerned with a process for synthesizing intermediates for compounds which inhibit the HIV protease. One desired intermediate is (1S,2R) indanyl epoxide substantially free of its undesired enantiomer (1R, 2S) indanyl epoxide. Another desired intermediate is (1S, 2R)-indandiol substantially free of its undesired enantiomer (1R,2S)-indandiol.

In this invention, a process is described for synthesizing quantitatively (1S,2S) bromo-indanol from indene, comprising the steps of
 (a) providing a mixture of one equivalent of indene, and an excess of a source of bromide ions, and haloperoxidase in buffer of pH between about 5.0 and about 8.0;
 (b) slowly mixing thereto between about one and about two equivalents of $H_2O_2$ and incubating the resulting second mixture until substantially all of the indene is consumed;
 (c) to give (1S,2S)-bromo-indanol.

In this invention, another process is described for synthesizing quantitatively (1S,2S) bromo-indanol from indene, comprising the steps of
 (a) providing a mixture of one equivalent of indene, and haloperoxidase in buffer of pH between about 5.0 and about 8.0;
 (b) slowly mixing thereto a second mixture of an excess of a source of bromide ions and between about one and about two equivalents of $H_2O_2$, and incubating the resulting third mixture until substantially all of the indene is consumed;
 (c) to give (1S,2S)-bromo-indanol.

In this invention, another process is described for synthesizing quantitatively (1S,2R) indanyl epoxide from indene, comprising the steps of
 (a) providing a mixture of one equivalent of indene, and an excess of a source of bromide ions, and haloperoxidase in buffer of pH between about 5.0 and about 8.0;
 (b) slowly mixing thereto between about one and about two equivalents of $H_2O_2$ and incubating the resulting second mixture until substantially all of the indene is consumed;
 (c) raising the pH to between about 9.0 and about 13.0;
 (d) to give (1S,2R) indanyl epoxide.

In this invention, another process is described for synthesizing quantitatively (1S,2R) indanyl epoxide from indene, comprising the steps of
 (a) providing a mixture of one equivalent of indene, and haloperoxidase in buffer of pH between about 5.0 and about 8.0;
 (b) slowly mixing thereto a second mixture of an excess of a source of bromide ions and between about one and about two equivalents of $H_2O_2$, and incubating the resulting third mixture until substantially all of the indene is consumed;
 (c) raising the pH to between about 9.0 and about 13.0;
 (d) to give (1S,2R) indanyl epoxide.

In this invention, another process is described for synthesizing quantitatively (1S,2R) indandiol from indene, comprising the steps of
 (a) providing a mixture of one equivalent of indene, and an excess of a source of bromide ions, and haloperoxidase in buffer of pH between about 5.0 and about 8.0;
 (b) slowly mixing thereto between about one and about two equivalents of $H_2O_2$ and incubating the resulting second mixture until substantially all of the indene is consumed;
 (c) raising the pH to between about 9.0 and about 13.0;
 (d) lowering the pH to between about 6.5 and about 3.0;
 (e) to give (1S,2R) indandiol.

In this invention, another process is described for synthesizing quantitatively (1S,2R) indandiol from indene, comprising the steps of
 (a) providing a mixture of one equivalent of indene, and haloperoxidase in buffer of pH between about 5.0 and about 8.0;
 (b) slowly mixing thereto a second mixture of an excess of a source of bromide ions and between about one and about two equivalents of $H_2O_2$, and incubating the resulting third mixture until substantially all of the indene is consumed;
 (c) raising the pH to between about 9.0 and about 13.0;
 (d) lowering the pH to between about 6.5 and about 3.0;
 (e) to give (1S,2R) indandiol.

The buffer may be a phosphate buffer, preferably with a pH between about 6.5 and about 7.5. The haloperoxidase may be a suspension of fungal cells containing the enzyme haloperoxidase. The haloperoxidase also may be a supernatant of a fungal cell culture containing the enzyme haloperoxidase. The haloperoxidase may be resuspended after ammonium salt precipitation of fungal cell culture supernatant containing haloperoxidase, wherein the resuspension contains the enzyme haloperoxidase. The fungal cells may be *Curvularia protuberata* MF 5400, or may be derived from ATCC 74332. The source of bromide ions may be NaBr or KBr or mixture thereof.

Another process of synthesizing quantitatively (1S,2S) bromo-indanol from indene, comprises the steps of
 (a) providing a mixture of one equivalent of indene and an excess of KBr, and *Curvularia protuberata* MF 5400 haloperoxidase in phosphate buffer of pH of about 7.0;
 (b) slowly mixing thereto between about one and about two equivalents of $H_2O_2$ and incubating the resulting second mixture until substantially all of the indene is consumed;
 (c) to give (1S,2S)-bromo-indanol.

Another process of synthesizing quantitatively (1S,2S) bromo-indanol from indene, comprises the steps of
 (a) providing a mixture of one equivalent of indene, and *Curvularia protuberata* MF 5400 haloperoxidase in phosphate buffer of pH of about 7.0;
 (b) slowly mixing thereto a second mixture of an excess of KBr and between about one and about two equivalents of $H_2O_2$, and incubating the resulting third mixture until substantially all of the indene is consumed;
 (c) to give (1S,2S)-bromo-indanol.

Another process for synthesizing quantitatively (1S,2R) indanyl epoxide from indene, comprises the steps of
 (a) providing a mixture of one equivalent of indene and an excess of KBr, and *Curvularia protuberata* MF 5400 haloperoxidase in phosphate buffer of pH of about 7.0;
 (b) slowly mixing thereto between about one and about two equivalents of $H_2O_2$ and incubating the resulting second mixture until substantially all of the indene is consumed;
 (c) raising the pH to about 12.5;
 (d) to give (1S,2R) indanyl epoxide.

Another process for synthesizing quantitatively (1S,2R) indanyl epoxide from indene, comprises the steps of
 (a) providing a mixture of one equivalent of indene, and *Curvularia protuberata* MF 5400 haloperoxidase in phosphate buffer of pH of about 7.0;
 (b) slowly mixing thereto a second mixture of an excess of KBr and between about one and about two equivalents of $H_2O_2$, and incubating the resulting third mixture until substantially all of the indene is consumed;

(c) raising the pH to about 12.5;

(d) to give (1S,2R) indanyl epoxide.

Another process for synthesizing quantitatively (1S,2R) indandiol from indene, comprises the steps of (a) providing a mixture of one equivalent of indene, and an excess of KBr, and *Curvularia protuberata* MF 5400 haloperoxidase in phosphate buffer of pH of about 7.0;

(b) slowly mixing thereto between about one and about two equivalents of $H_2O_2$ and incubating the resulting second mixture until substantially all of the indene is consumed;

(c) raising the pH to about 12.5;

(d) lowering the pH to about 5.0;

(e) to give (1S,2R) indandiol.

Another process for synthesizing quantitatively (1S,2R) indandiol from indene, comprises the steps of (a) providing a mixture of one equivalent of indene, and *Curvularia protuberata* MF 5400 haloperoxidase in phosphate buffer of pH of about 7.0;

(b) slowly mixing thereto a second mixture of an excess of KBr, and between about one and about two equivalents of $H_2O_2$, and incubating the resulting third mixture until substantially all of the indene is consumed;

(c) raising the pH to about 12.5;

(d) lowering the pH to about 5.0;

(e) to give (1S,2R) indandiol.

In the practice of this invention, the enzymatic reaction of the haloperoxidase enzyme with substrate indene is initiated by the slow addition or feeding of $H_2O_2$ to the mixture containing the haloperoxidase. Rapid addition of $H_2O_2$ will inactivate the enzyme. The source of bromide ions may be mixed first with enzyme and substrate, or it may be mixed first with $H_2O_2$. In any case, the mixture comprising $H_2O_2$ should be added last. Indene may be added directly or as a solution in solvent.

The buffer of the haloperoxidase reaction is an aqueous buffer having a pH between about 5.0 and about 8.0, preferably phosphate buffer of pH about between about 6.5 and about 7.5, most preferably of pH about 7.0.

The concentration of substrate indene is typically about 1 g/L. It is understood by the skilled artisan that substrate concentration can be varied according to standard and conventional techniques. As the haloperoxidase reaction proceeds, substrate is consumed. Substantially all of the indene disappears in about 2 hours, but variations in incubation time of the enzymatic reaction may occur. Temperature of the enzymatic reaction is typically room temperature, but the reaction can be carried out at other temperatures, e.g., between about 15° C. to about 37° C.

The enzymatic product is predominantly (2S,1S)-bromoindanol. This product is then subjected to alkaline treatment to give (1S,2R)-indanyl epoxide. In this chemical step, the pH is raised to between about 9.0 and about 13.0, preferably about 12.5. This chemical conversion to a chiral epoxide intermediate is typically rapid, e.g., reaction is often complete in less than 10 minutes.

The second chemical step converts (1S,2R)-indanyl epoxide to (1S,2R)-indandiol by lowering the pH to between about 6.5 and about 3.0, preferably to about 5.0. The lower the pH, the more rapid the reaction.

In the bioconversion step of the present invention, quantitative formation of (2S,1S)-bromo-indanol from substrate indene is carried out by any suitable haloperoxidase. The haloperoxidase may be a neutral haloperoxidase or an alkaline haloperoxidase. One preferred haloperoxidase source is the fungus *Curvularia protuberata* MF 5400 or ATCC 74332. The bioconversion step is conveniently carried out with unpurified or partially purified enzyme, e.g., with a suspension of fungal cells, with a supernatant from a fungal cell culture or with a resuspension of an ammonium sulfate precipitation of fungal culture cell supernatant containing haloperoxidase.

The source of bromide ions is any suitable source, preferably NaBr or KBr or mixture thereof. Chloride ions were found essentially not to produce product.

Conversion of Indene to Indan Epoxide and Indandiols

The commercially available acidic chloroperoxidase from *Calderiomyces fumago* catalyzes the synthesis of indan oxide (epoxide) from indene in the presence of hydrogen peroxide under acidic conditions. However, the epoxides obtained are racemic.

Since the acidic haloperoxidase (chloroperoxidase) acts on indene to produce epoxides when $H_2O_2$ is slowly fed to the system (to avoid inhibition of the enzyme), the neutral haloperoxidase preparations from various cultures were tested under similar conditions except that the reaction pHs were maintained around 7. However, no indene bioconversion could be detected, even with the $(NH_4)_2SO_4$-concentrated enzymes under various $H_2O_2$-feeding conditions.

It was discovered by applicants that indene bioconversion by these neutral haloperoxidases only took place when bromide ions were co-fed to the system. Importantly, it was found that bromohydrins were stable under neutral conditions and could be easily converted to epoxides by raising pH to basic range (>12), despite the probable absence of halohydrin epoxidase in these cultures. Results showed that the epoxides formed were not always racemic, depending on the culture used. Thus a novel method was established for screening chiral epoxide-synthesizing activity from these cultures. When chloride ions were used to replace bromide, very little chloro-indanol formation was observed.

Nine cultures with relatively high neutral haloperoxidase activities were tested using either broth supernatant or $(NH_4)_2SO_4$ precipitate. The concentrated preparation of the fungus *Curvularia protuberata* MF 5400 was found to catalyze primarily the synthesis of trans-2S-bromo-1S-indanol, which after raising the pH to about 12 resulted in the formation of the desired 1S,2R-epoxide with 85% enantiomeric excess (ee). Applicants have also found that the conversion to epoxides at basic pH was quantitative. All other cultures produced the two trans-bromohydrins at equal ratio, and therefore racemic epoxides.

It was also found that the reaction pH plays an important role in bromohydrin and thus epoxide yield and chirality achieved by the fungus *Curvularia protuberata* MF 5400. Within a pH range of 5.5 to 7.5, higher pH favored ee, while lower pH accelerated bioconversion.

The preferred bioconverting microorganism is the fungus *Curvularia protuberata* MF 5400, deposited at the American Type Culture Collection (ATCC 74332).

ATCC Deposit 74322

Before the U.S. filing date of the present application, a sample of the microorganism the fungus *Curvularia protuberata* MF 5400 was deposited at the American Type Culture Collection (ATCC), 12301 Parklawn Drive, Rockville, Md. 20852. The culture access designation is ATCC 74332. Application for conversion to a Budapest Treaty deposit was applied for on or about Mar. 16, 1995. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

General Characteristics of ATCC 74332

The physical characteristics and taxonomy, including morphological, cultural, biological and physiological characteristics are briefly described hereinbelow.

*Curvularia protuberata* MF 5400, Nelson and Hodge: NRRL 4671 is previously referred to in NRRL catalogs and elsewhere as *Biplolaris sp*.

In agar culture, colonies of NRRL 4671 exhibit the following morphology:

Colonies on oatmeal agar at 25° C., 12 hr photoperiod attaining 48 mm in 7 days, raised, with advancing zone appressed, margin even, with aerial mycelium velvety to lanose, dull, zonate, at dull yellow to yellowish brown, then ochraceous orange, soon gray to dark gray, and finally black at onset of sporulation, with reverse dull grayish brown, exudates absent. Stromata not observed.

Colonies on YM agar at 25° C., 12 hr photoperiod attaining 32–36 mm in 7 days, raised, velvety to lanose, with margin undulating, appressed, hyaline to pale yellowish brown, soon becoming gray, and finally olivaceous black with onset of sporulation, with reverse dull yellowish brown to olivaceous black. Stromata not observed.

Conidiophores up to 500 μm tall, up to 7 μm wide, arising directly from agar surface, straight to flexuous, becoming geniculate-nodose towards apex, usually unbranched, smooth-walled, septate, yellowish brown to olivaceous brown in lactophenol. Conidiogenous cells sympodial, integrated, polytretic, smooth, with conidiogenous loci cicatrized.

Conidia 26–43 μm long, 11–14 μm wide, broadly fusiform to clavate, often distinctly curved, smooth-walled, usually 4-septate, but sometimes 3-septate, with median cell often swollen and/or curved, with basal and terminal cells usually paler in color, with a distinctly protuberant hilum, with hilum extending up to 1.5 μm. Conidia germination occurring in 12 hr or less on cornmeal dextrose agar, with first germ tube or microconidium arising from apical cell, and second germ tube from basal cell. Microconidia arising from apical cell of conidia or first-formed germ tube, 10–21 μm long, 6–8 μm wide, 1–3 septate, pyriform to broadly fusiform.

*Curvularia spp.* (J. B. Ellis. 1971. Dematiaceous Hyphomycetes. Commonwealth Mycological Institute, Kew, United Kingdom; A. Sivanesan. 1987. Graminicolous species of Bipolaris, Curvularia, Drechslera, Exserohilum and their teleomorphs. *Mycological Paper* 157:1–261) can generally be distinguished from the similar genera Exserohilum and Dreschlera, by curved conidia and polar conidial germination. Most authorities recognize no clear distinction between Curvularia and Bipolaris, hence a possible reason for the assignment to Bipolaris. Within Curvularia, this isolate was determined as *C. protuberata* because of its conidia with a protuberant hilum, and predominantly 4-septate conidia that may be more than 40 μm long.

General Description of Culture Conditions

The preferred source of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of cells in massive amounts, submerged aerobic cultivation conditions are preferred. For the production in small amounts, a shaking or surface culture in a flask or bottle is employed. Furthermore, when the growth is carried out in large tanks, it is preferable to use the vegetative forms of the organism for inoculation in the production tanks in order to avoid growth lag in the process of production. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is generally autoclaved to sterilize the medium prior to inoculation. The pH of the medium is generally adjusted to about 5.5 prior to the autoclaving step.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°–35° C., for a period of about 5 to 12 days, which may be varied according to fermentation conditions and scales. Preferably, the production cultures are incubated for about 10 days at 28° C. on a rotary shaker operating at 220 rpm.

Preferred culturing/production media for carrying out the fermentation include the following media:

| | g/L |
|---|---|
| YME | |
| Malt Extract | 20 |
| Yeast Extract | 3 |
| Glucose | 3 |
| CFM | |
| Potato Dextrose Broth | 24 |
| Yeast Extract | 3 |
| CFM microelement solution | 1 ml |
| MOPS buffer, and sodium hydroxide to bring pH up to 7.0 | 20 |
| Microelement solution contains: | |
| $KH_2PO_4$, | 0.8 |
| $CuSO_4 \cdot 5H_2O$ | 0.64 |
| $FeSO_4 \cdot 7H_2O$ | 0.11 |
| $MnCl_2 \cdot 4H_2O$ | 0.8 |
| $ZnSO_4 \cdot 7H_2O$ | 0.15 |

Product Recovery

The product cis (1S,2R) indandiol can be recovered from buffer by conventional means which are commonly used for the recovery of other known substances. The substances produced are found in the buffer, and accordingly can be isolated and purified by conventional methods such as concentration under reduced pressure, lyophilization, extraction with a conventional solvent, such as ethyl acetate and the like, pH adjustment, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), crystallization, recrystallization, and the like. A preferred method is solvent extraction, particularly using ethyl acetate.

Formulations

The product compounds synthesized from the intermediates of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The processes and intermediates of this invention are useful for the preparation of end-product compounds that are useful in the inhibition of HIV protease, the prevention or treatment of infection by the human immunodeficiency virus (HIV), and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds, including their use as controls. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

HIV protease inhibitor compounds that can be made from the intermediates and processes of the instant invention are disclosed in EPO 541,168. The HIV protease inhibitory compounds may be administered to patients in need of such treatment in pharmaceutical compositions comprising a pharmaceutical carrier and therapeutically-effective amounts of the compound or a pharmaceutically acceptable salt thereof. EPO 541,168 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included in the present invention. A mixture of enantiomers includes a 1:1 mixture, as well as any other mixture, e.g., 1:4, 4:3, 2:1.

Representative experimental procedures utilizing the novel process are detailed below. These procedures are exemplary only and are not limitations on the novel process of this invention.

EXAMPLE 1

Organisms and Culture Conditions

Fungal strains from high salt environments (e.g., desert, marsh, marine, etc.) were maintained on slants of YMA medium (composition in gm/L: malt extract, 10; yeast extract, glucose, 4; agar, 20; 10 ml trace element solution; pH adjusted to 7.0). The trace element solution consisted of (in gm/L of 0.6N HCl): $FeSO_4 \cdot 7H_2O$, 1.0; $MnSO_4 \cdot H_2O$, 1.0; $CuCl_2 \cdot 2H_2O$, 0.025; $CaCl_2 \cdot 2H_2O$, 0.10; $H_3BO_3$, 0.056; $ZnSO_4 \cdot 7H_2O$, 0.20; and, $(NH_4)_6Mo_7O_{24} \cdot 4H_2O$. Growth from a slant culture (ca. 1 cm$^2$) was used to inoculate a 250 ml Erlenmeyer flask containing 25 ml of KF seed medium (composition in gm/L: corn steep powder, 5; tomato paste, 40; oat flour, 10; glucose, 10, 10 ml trace element solution; pH adjusted to 6.8). Seed cultures were incubated for 2 to 3 days at 28° C. with 220 rpm shaking. One milliliter of seed culture was used to inoculate each 250 ml Erlenmeyer flask containing 25 ml of a modified CFM production medium essentially as described by Hunter-Cevera and Sotos (*Microb. Ecol.*, 1986. 12:121–127). CFM production medium is composed of (in gm/L): potato dextrose broth, 24; yeast extract, 3; MOPS buffer, 15; agar, 2; 1 ml microelement solution; pH adjusted to 7.0. The microelement solution consisted of (in gm/L): $K_2HPO_4$, 0.8; $CuSO_4 \cdot 5H_2O$, 0.64; $FeSO_4 \cdot 7H_2O$, 0.11; $MnCl_2 \cdot 4H_2O$, 0.8; and, $ZnSO_4 \cdot 7H_2O$, 0.15. Production cultures were incubated for specified periods of time at 28° C. with 220 rpm shaking.

EXAMPLE 2

Haloperoxidase Assay

A phenol red based assay was employed essentially as previously described by Hunter-Cevera and Sotos (*Microb. Ecol.*, 1986. 12:121–127). Prior to assaying, whole broth from a production flask was homogenized to ensure uniformity. Two-milliliters each of whole broth and phenol red reagent were combined and the haloperoxidase reaction was started by the addition of 0.010 ml of 3% (v/v) hydrogen peroxide. A second reaction omitting the hydrogen peroxide was used as a blank. Reaction mixtures were incubated at 28° C. and additional 0.010 ml aliquots of 3% hydrogen peroxide was added after 2 and 4 hours followed by brief vortexing. After incubation over-night, reaction mixtures which were visibly blue (compared to the blank) were centrifuged to remove cell mass. The absorbance of the supernatant at 595 nanometers compared to the blank was measured to determine a relative amount of haloperoxidase activity.

EXAMPLE 3

Haloperoxidase Production in 2-liter Erlenmeyer Flasks

Fungal strains identified in the screen as producing neutral haloperoxidase were re-cultivated in 2-liter Erlenmeyer flasks containing 500 ml of CFM medium. The flasks were inoculated with 20 ml of a 72-hour culture and were incubated at 28° C. on an orbital shaker at 180 rpm. Samples (10 ml) were removed from the flask and were centrifuged for 15 minutes at 3000 rpm in a table top centrifuge. A volume of 5 ml of supernatant was mixed with 5 ml of phenol red solution and incubated at 25° C. An amount of 20 ul of a 0.3% $H_2O_2$ solution was added to the reaction at 0, 1, 2, and 3 hours. After 24 hours of incubation at 25° C., the optical absorbance of the assay mixture was determined as previously described. A unit of haloperoxidase is defined as the amount of enzyme catalyzing an increase of 1 OD unit at 595 nanometers, when employing the conditions previously described.

EXAMPLE 4

Enzyme Preparation

Cultures identified in the phenol-red screen as having neutral haloperoxidase activity were harvested by centrifuging the whole broth and collecting the culture supernatant (pH around neutral). The concentrated preparation was obtained by adding ammonium sulfate (80% saturation) to broth supernatant, redissolving the precipitate in 0.1M phosphate buffer (pH 7), and filtering to remove black pigment insolubles. The concentrated preparations normally gave a 3 to 5-fold increase in enzyme activity as analyzed by phenol-red Assay. The preparations were stored at 4° C. until use.

EXAMPLE 5

Indene Bioconversion

Reaction was typically carried out in a 20-mL scintillation vial at ambient temperature and with a magnetic stir-bar stirring at 500 rpm. To 5 ml of enzyme preparation was added 0.05 ml of 10% (v/v) indene in acetone to give 1 g/L initial substrate concentration. The reaction was initiated by starting a feed of $H_2O_2$ at 0.8 mM/min and KBr at 0.4 mM/min by means of a syringe pump (2.7 ml/h of a stock solution of 88 mM $H_2O_2$ and 44 mM KBr). The vial was always sealed with parafilm except during sampling. Feeding was stopped after 1 to 2 hours of reaction, and after sampling the pH of the mixture was adjusted to 12 using 50% NaOH. Agitation was continued for another 5 minutes and the mixture was then extracted for analysis.

EXAMPLE 6

Analysis

Samples taken prior to basification were extracted with an equal volume of hexane/ethanol (95/5) through vigorous vortexing, and 0.5 ml from the solvent layer was further diluted by one-fold with the same solvent. Normal phase HPLC was used to detect indene and bromo-indanols. The system consisted of a solvent delivery pump, an autosampler, a column (amylose tris (3,5-dimethylphenyl carbamated) coated on a 10 μm silica gel substrate, 4.6×25) and a UV detector set at 220 nm. The mobile phase was comprised of 92% hexane and 8% ethanol at a flow rate of 1.0 ml/min.

Half of the sample taken after basification was treated and analyzed the same way as described above to monitor the conversion of bromo-indanols to epoxides. The other half of the sample was extracted with hexane only. The 1S,2R- and 1R,2S-epoxides in the hexane-extracted samples were separated by normal phase HPLC using a column (cellulose tribenzoate coated on a 10 μM silica-gel substrate, 4.6 ×25). The mobile phase was 97% hexane and 3% isopropanol with a 1.0 ml/min flow rate. The eluent was monitored at 230 nm. Enantiomeric excess was calculated based on the peak areas of the two epoxides.

Assay for the chiral diol follows. The (1S,2R) and (1R,2S) indandiols were separated, employing a column (amylose tris (3,5-dimethylphenyl carbamate) coated on a 10 μm silica-gel substrate). The mobile phase (92% hexane, 8% ethanol) was delivered at a rate of 1 ml/min at room temperature. Detection was performed at 220 nm. Typically (1R,2S)-indandiol and (1S,2R) indandiol elute 12 min and 14 min after injection, respectively.

EXAMPLE 7

Haloperoxidase Screening

About 350 to 400 fungal strains were evaluated for their ability to produce neutral haloperoxidase. Most of these fungi were isolated from high salt environments (e.g., desert, marsh, marine, etc.), a proven habitat for neutral haloperoxidase producers. Table 1 lists the fungi that were found to produce significant amounts of haloperoxidase. Haloperoxidase production kinetics was studied for two selected organisms: maximum haloperoxidase activity was achieved after 8 days and 18 days for *Biplolaris sp.* (MF 5400) (also known as *Curvularia protuberata* MF 5400) and for *Curvularia protuberata* (JP 547), respectively.

TABLE 1

| Fungal strains producing alkaline haloperoxidase. | |
|---|---|
| SPECIES | STRAIN |
| *Curvularia lunata* | MF 5395 |
| *Alternaria sp.* | GB 3432 |
| *Curvularia lunata* | GB 1736 |
| *Pestalotiopsis sp.* | CR 538 |
| Unidentified fungus | MF 4715 |
| *Curvularia sp.* | MF 4697 |
| *Bipolaris sp.* | MF 5400 |
| *Ulocladium sp.* | NRRL 15200 |
| *Cochliobolus lunatus* | NRRL 15293 |
| *Curvularia protuberata* | JP 547 |
| *Ulocladium chartarum* | ATCC 18045 |
| *Drechslera haloides* | ATCC 28856 |
| *Curvularia lunata* | MF 5572 |

EXAMPLE 8

A. Conversion of Indene Oxide to Cis-1-Amino-2-Indanol

| Materials | Mol. Wt. | Grams or ml | Millimoles |
|---|---|---|---|
| Indene oxide | 132 | 1 ml | 8.33 |
| Acetonitrile | 41 | 10 ml | 244 |
| Water | 18 | 2.15 ml | 119.4 |
| Conc. $H_2SO_4$ | 98 | 0.92 ml | 16.6 |
| 5N KOH | 57 | 3.0 ml | 15 |
| Dowex 50 × 4 (H+) | 1.9 meq/ml | 15 ml wet resin | 28.5 meq |
| Methanol | 17 | 50 ml | 50 |

To one ml of indene oxide (8.33 mmoles) dissolved in 10 ml acetonitrile was added 0.15 ml water (8.33 mmoles). The mixture was cooled to 0°–5° in an ice bath. Concentrated sulfuric acid was added dropwise while maintaining the batch temperature below 10°. When all the acid was added and the temperature was allowed to rise to 20°–25°. The clear solution was aged for 30 minutes.

To this mixture was added 2 ml of water and the solution heated for 30 minutes. When the methyl oxazoline was completely coverted to cis amino indanol the reaction mixture was cooled to room temperature.

A solution of 5N KOH (3 ml, 15 mmoles) was added. This is 90% of theory for the sulfuric acid. The solution remained acid to litmus. If the pH rises above, 2 re-acylation occurs and the yield of amino indanol is reduced. The white solid ($K_2SO_4$) was removed by filtration.

Dowex resin 15 ml (wet with acetonitrile) was added with stirring. The stirred resin was aged for 15 minutes and sampled for LC (dilx 50). When the LC peak for amino indanol disappeared, the resin was collected by filtration, washed with acetonitrile and then with methanol.

The wet resin was treated with a solution of 50 ml 1N $NH_3$ in methanol and the slurry stirred at room temperature for 30 minutes. The resin was again collected by filtration and the methanol/$NH_3$ saved. Another charge of 1N $NH_3$/MeOH (20 ml) was added and the resin reslurried. After removal of the resin the methanol/$NH_3$ solutions of the amino indanol were combined and concentrated to remove the $NH_3$. Analysis of the final MeOH solution shows 1.0 g (81% yield) cis-1-amino-2-indanol ready for the tartaric acid resolving agent.

B. Preparation of Racemic Indene Oxide

Indene (95%, 122 mL) was dissolved in methanol (812 mL) and acetonitrile (348 mL), then filtered. The filtrate was diluted with 0.05 M sodium dibasic phosphate (116 mL), then adjusted to pH 10.5 with 1 M aqueous sodium hydroxide. Aqueous hydrogen peroxide (35%, 105 mL) was diluted with water (53 mL) and added over 3 h, while maintaining the temperature at 25° C. and the internal pH at 10.5 with 1 M aqueous sodium hydroxide (120 mL total).

After 6 h, 1 M aqueous sodium metabisulfite was added (26 mL), while maintaining the pH above 8.3 by addition of 1 M aqueous NaOH (39 mL). Water (700 mL) was added and the mixture extracted with methylene chloride (580 mL and 300 mL). The combined organic extracts containing indene oxide (117 g) were concentrated to a volume of 600 mL.

C. Preparation of (1S, 2R)-indene oxide

The substrate, (1S, 2R)-indene oxide is prepared according to the method described by D. J. O'Donnell, et at., *J. Organic Chemistry*, 43, 4540 (1978), herein incorporated by reference for these purposes.

D. Preparation of cis-1-amino-2-indanol

Indene oxide (117 g) diluted to a total volume of 600 mL in methylene chloride was diluted with acetonitrile (600 mL) and cooled to −20° C. Methanesulfonic acid (114 mL) was then added. The mixture was warmed to 25° C. and aged for 2 h. Water (600 mL) was added and the mixture heated at 45° C. for 5 h. The organic phase was separated and the aqueous phase further heated at reflux for 4 h with concentration to approximately 200 g/L. The solution was adjusted to pH 12.5 with 50% aqueous sodium hydroxide, and then cooled to 5° C. and filtered, dried in vacuo, to provide cis-1-amino-2-indanol.

E. Preparation of 1S-amino-2R-indanol (1,S, 2R)-indene oxide (85% ee,) (250 g, 0.185 mole) was dissolved in chlorobenzene (300 mL) and heptanes (1200 mL) and slowly added to a solution of methanesulfonic acid (250 mL, 0.375 mole) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C. for 2–3 h then cooled to room temperature. Chlorobenzene (1000 mL) was added, the mixture stirred, the organic phase separated. The remaining aqueous phase containing 1S-amino, 2R-indanol (85% ee, 165 g, 60%) was adjusted to pH 12 with 50% aqueous sodium hydroxide and the product collected by filtration and dried in vacuo at 40° C. to yield 1S-amino, 2R-indanol (85% ee, 160 g).

F. Preparation of 1S-amino-2R-indanol (1S, 2R)-indene oxide (85% ee,) (250 g, 0.185 mole) was dissolved in chlorobenzene (300 mL) and heptanes (1200 mL) and slowly added to a solution of fuming sulfuric acid (21% $SO_3$, 184 mL) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C. for 2–3 h, then cooled to room temperature. Chlorobenzene (1000 mL) was added, the mixture stirred, the organic phase separated. The remaining aqueous phase containing 1S-amino, 2R-indanol (85% ee, 205 g, 74%) was diluted with an equal volume of acetonitrile. The pH was adjusted to 12.5 with 50% aqueous sodium hydroxide and the organic phase separated. The remaining aqueous phase was extracted with additional acetonitrile. The combined acetonitrile extracts were concentrated in vacuo to provide 1S-amino, 2R-indanol (85% ee, 205 g).

Alternatively, the remaining aqueous phase containing 1S-amino-2R-indanol (85% ee, 205 g, 74%) was diluted with an equal volume of butanol and the pH was adjusted to 12.5 with 50% aqueous sodium hydroxide and the organic phase separated. The organic phase was washed with chlorobenzene. L-tartaric acid was added and water was removed by distillation to crystallize the tartaric acid salt of the amino-indanol.

G. Use of Benzonitrile

Indene oxide (5 g) was dissolved in benzonitrile (50 mL) at 25° C. and sulfuric acid (98%, 2.25 mL) was added. The mixture was diluted with 5 M aqueous sodium hydroxide solution (50 mL) and extracted with methylene chloride. The organic extracts were concentrated in vacuo to give 5.03 g of oxazoline.

H. Resolution of cis-1-Amino-2-indanol

Cis-1-Amino-2-indanol (100 g) was dissolved in methanol (1500 mL) and a solution of L-tartaric acid (110 g) in methanol (1500 mL) was added. The mixture was heated to 60° C. and cooled to 20° C., filtered and dried in vacuo to give 1S-amino, 2R-indanol L-tartaric acid salt as a methanol solvate (88 g).

J. Preparation of 1S-Amino-2R-indanol

1S-Amino, 2R-indanol L-tartaric acid salt methanol solvate (88 g) was dissolved in water (180 mL) and heated to 55°–60° C. The solution was clarified by filtration and the pH adjusted to 12.5 with 50% aqueous sodium hydroxide. The mixture was cooled to 0°–5° C. over 2 h, then aged at that temperature for 1 h, filtered, washed with cold water and dried in vacuo at 40° C. to yield 1S-amino, 2R-indanol (100% ee, 99% pure, 37 g).

K. Conversion of 1,2 indanol to cis-1-amino-2-indanol

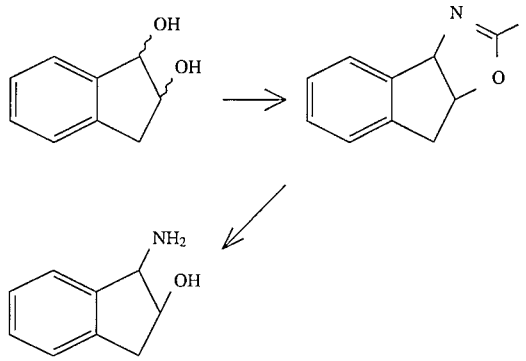

| Materials | Mol Wt | Grams or ml | Millimoles |
|---|---|---|---|
| 1,2 indane diol | 150 | 300 mg. | 2 |
| acetonitrile | 41 | 2.5 ml | 47.3 |
| water | 18 | 0.04 ml | 2 |
| sulfuric acid | 98 | 0.22 ml | 4 |
| 5N KOH | 57 | 1.6 ml | 8.0 |
| Dowex 50 × 4 (H+) | | 10 ml | |
| methanol (1 m NH3) | | 30 ml | |

To 300 mg indane diol dissolved in 3 ml of acetonitrile containing 0.04 ml water was added dropwise at 0°–10° C. a volume of 0.22 ml of concentrated $H_2SO_4$. After the addition was complete the ice bath was removed and the batch warmed to room temperature. After a 30 minute age the clear solution was sampled for Ic assay (dilx 500). When all the glycol was consumed, the solution was treated further with water and heated to reflux on a steam bath to hydrolyze the oxazoline.

L. Preparation of cis-1S-amino-2R-indanol from cis-(1S,2R)indandiol

Cis-(1S,2R)-indandiol (1 g) was dissolved in acetonitrile (10 mL), cooled to 0° C. and concentrated sulfuric acid (1.0 mL) was added. The mixture was aged for 40 minutes with warming to 20° C. Water (0.8 mL) was added and the mixture was heated to reflux. Aqueous 5 M potassium hydroxide (1.6 mL) was added to adjust the pH to more than 11 and the resulting solid (potassium sulfate) removed by filtration to provide an aqueous solution of the cis-1S-amino-2R-indanol (0.79 g, 66% yield).

M. Preparation of cis-1-amino-2-indanol from cis-1,2-indandiol

Cis-1,2-indandiol (1.0 g) was dissolved in acetonitrile (20 mL), cooled to –40° C., and fuming sulfuric acid (21% $SO_3$, 0.8 mL) was added. The mixture was aged for 1 hour with gradual warming to 0° C. Water was added and the mixture heated to 80° C. for 1 hour to provide an aqueous solution of cis-1-amino-2-indanol.

EXAMPLE 9

Preparation of Amide 9

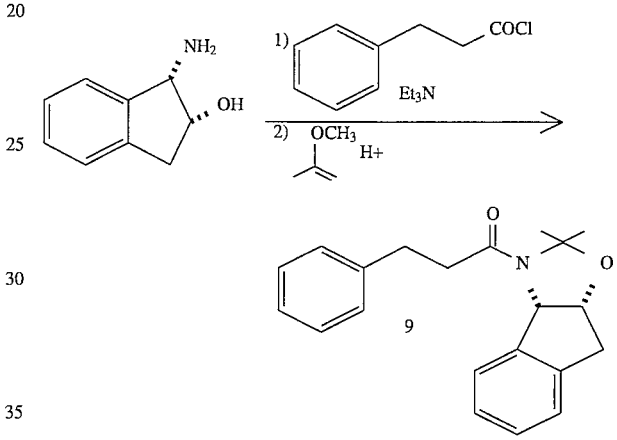

A solution of (–)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature between 14°–24° C. with an ice-water cooling batch. After addition, the mixture was aged at 18 to 20° C. for 30 minutes and checked by HPLC analysis for the disappearance of (–)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4$/$K_2HPO_4$), 1.0 mL/min., injection volume=20 mL, detection=200 nm, sample preparation=500 X dilution. Approximate retention times:

| retention time (min) | identity |
|---|---|
| 6.3 | cis-aminoindanol |

The reaction was treated with pyridinium p-toluene-sulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous NaHCO$_3$ (10 L). The mixture was agitated and the layers were separated. The ethyl acetate extract was washed with 5% aqueous NaHCO$_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 9 (86.4%, 98 area % by HPLC). $^1$H NMR (300.13 MHz, CDCl$_3$, major rotamer) δ 7.36–7.14 (m, 9 H), 5.03 (d, J=4.4, 1 H), 4.66 (m, 1 H), 3.15 (m, 2 H), 3.06 (br s, 2 H), 2.97 (m, 2 H), 1.62 (s, 3 H), 1.37 (s, 3 H); $^{13}$C NMR (75.5 MHz, CDCl$_3$, major rotamer) δ$_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1.

Analysis calculated for C$_{21}$H$_{23}$NO$_2$: C, 78.47; H, 7.21; N, 4.36.

Found: C, 78.65; H, 7.24; N, 4.40.

EXAMPLE 10

Preparation of Epoxide 11 Tosylate Method

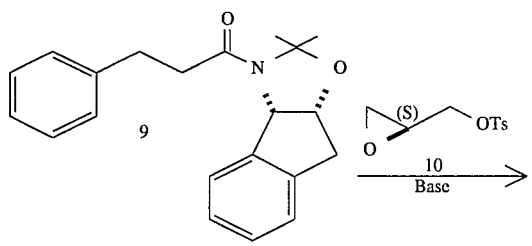

A solution of acetonide 9 (1000 g, 3.11 mol) and 2(S)-glycidyl tosylate 10 (853 g, 3.74 mol, 1.2 equiv.) in 15.6 L of THF (KF=22 mg/mL) in a 50 L 4-neck round bottom flask, equipped with a thermocouple, mechanical stirrer, addition funnel and nitrogen inlet adapter was degassed 3 times via vacuum-nitrogen purge and cooled to −56° C. Then, lithium hexamethyldisilazide (LiN[(CH$_3$)$_3$Si]$_2$)(2.6 L, 1.38 M, 1.15 equiv.) was added over 2 h, while keeping the internal temperature between −50° to −45° C. The reaction mixture was stirred at −45° to −40° C. for 1 h and then allowed to warm to −25° C. over 1 h. The mixture is stirred between −25° to −22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection= 254 nm, sample preparation=100×dilution. Approximate retention times:

| retention time (min) | identity |
| --- | --- |
| 5.5 | amide 9 |
| 6.5 | glycidyl tosylate 10 |
| 13.5 | epoxide 11 |

The reaction mixture wag quenched with DI water (6.7 L) at −15° C. and partitioned with ethyl acetate (10 L). The mixture was agitated and the layers were separated. The ethyl acetate extract was washed with a mixture of 1% aqueous NaHCO$_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 11 (61.2%, 98.7 area % of the major epoxide by HPLC). $^{13}$C NMR (300 MHz, CDCl$_3$) δ 171.1, 140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

EXAMPLE 11

Preparation of Penultimate 14

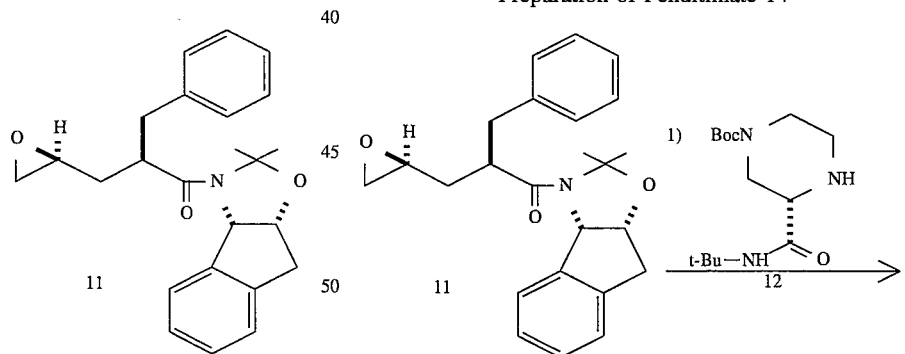

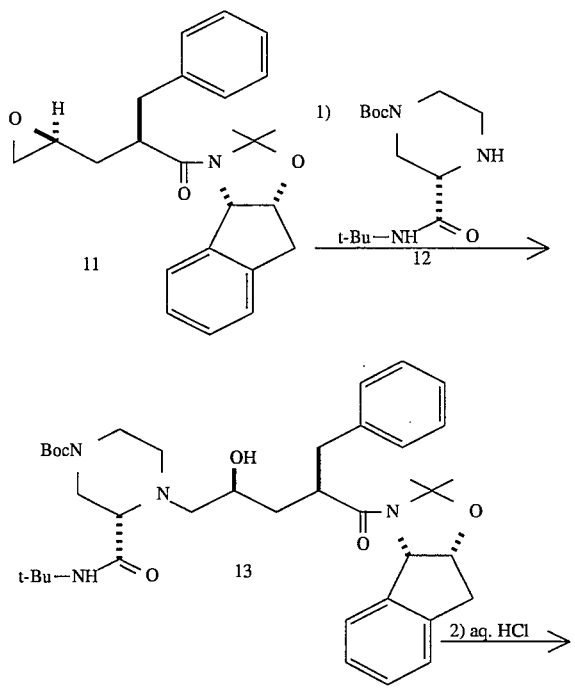

19
-continued

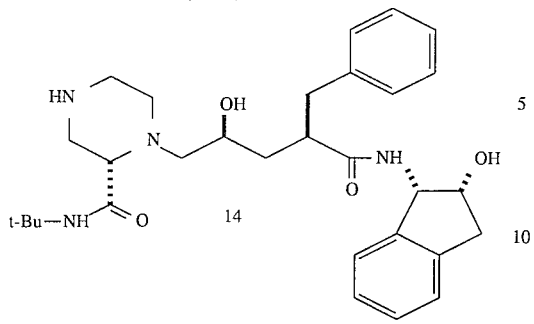

A slurry of the 2(S)-t-butylcarboxamide-4-N-Boc-piperazine 12 (1950 g, 6.83 mol, >99.5% ee) (ee×enantiomeric excess) and the epoxide 11 (2456 g, 97.5:2.5 mixture of 4 S/R epoxides, 6.51 mol) in isopropanol (2-propanol, 18.6 L) in a 72 L round bottom flask with four inlets, equipped with a mechanical stirrer, reflux condenser, steam bath, Teflon coated thermocouple and nitrogen inlet, was heated to reflux (internal temperature was 84°–85° C.). After 40 min, a homogeneous solution was obtained. The mixture was heated at reflux for 28 h.

The internal temperature during reflux was 84°–85° C. Progress of the reaction was monitored by HPLC analysis: 25 cm Dupont C8-RX column, 60:40 acetonitrile/10 mM ($KH_2PO_4/K_2HPO_4$), 1.0 mL/min., detection=220 nm, sample preparation=2 µL, reaction mixture diluted to 1 mL in acetonitrile. Approximate retention times:

| retention time (min) | identity |
| --- | --- |
| 4.8 | piperazine 12 |
| 8.9 | epoxide 11 |
| 15.2 | coupled product 13 |

After 28 h, the remaining epoxide 11 and coupled product 13 (by HPLC analysis) were 1.5 area % and 91–93 area %, respectively. The mixture was cooled to 0° to 5° C. and 20.9 L of 6 N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min) | identity |
| --- | --- |
| 7.0 | cis-aminoindanol |
| 11.9 | penultimate 14 |
| 15.1 | coupled product 13 |

The mixture was cooled to 0° C. and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF=1.8 mg/mL). The HPLC assay yield of 14 in ethyl acetate was 86.5%. The penultimate compound 14 in DMF was directly used in the next step without further purification. For isolated 14: $^{13}$C NMR (75.4 MHz, $CDCl_3$) δ 175.2, 20
170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 12

Preparation of Monohydrate of Compound J

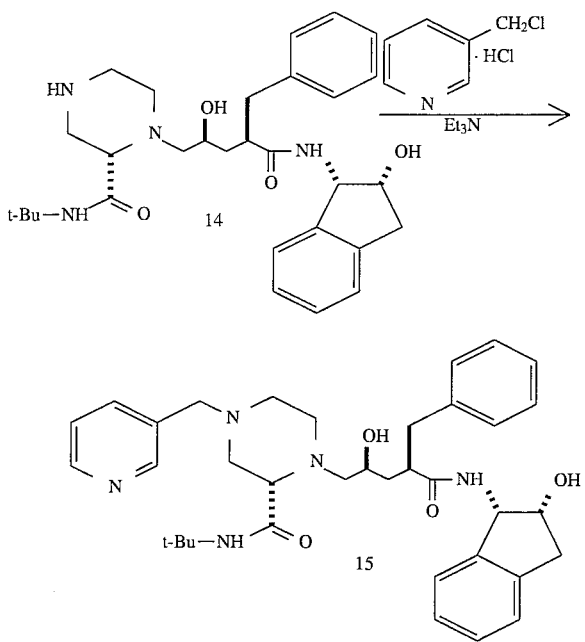

Compound J

The solution of 14 in DMF (10.5 L, KF=10 mg/mL) from the previous step was charged with 8 L of sieve dried DMF (KF.<30 mg/L) and the mixture was heated with a steam bath under vacuum of 30" of Hg to distill off mainly water and/or any residual isopropanol or ethyl acetate solvent. The final concentrate volume was 13.5 L (KF=1.8 mg/mL) and then triethylamine (2.86 L, 20.51 mol) was added to the 25° C. solution followed by 3-picolyl chloride hydrochloride (96%, 1287 g, 7.84 mol). The resulting slurry was heated to 68° C.

The progress of the reaction was followed by HPLC analysis using the same conditions as the previous step. Approximate retention times:

| Retention time (min) | Identity |
| --- | --- |
| 2.7 | DMF |
| 4.2 | 3-picolyl chloride |
| 4.8 | Compound J |
| 9.1 | penultimate 14 |

The mixture was aged at 68° C. until the residual penultimate compound 14 was <0.3 area % by HPLC analysis.

The mixture was stirred at 68° C. for 4 h, then cooled to 25° C. and partitioned with ethyl acetate (80 L) and a mixture of 24 L of saturated aqueous $NaHCO_3$ and distilled water (14 L). The mixture was agitated at 55° C. and the layers were separated. The ethyl acetate layer was washed three times with water (20 L) at 55° C. The washed ethyl acetate layer is concentrated at atmospheric pressure to a final pot volume of 30 L. At the end of the atmospheric concentration, water (560 mL) was added to the hot solution and the mixture was cooled to 55° C. and seeded with Compound J monohydrate. The mixture was cooled to 4° C. and filtered to collect the product. The product was washed with cold ethyl acetate (2×3 L), and dried at house vacuum at 25° C. to afford 2905 g (70.7%) of Compound J monohydrate as a white solid.

EXAMPLE 13

Pyrazine-2-tert-butyl-carboxamide 17

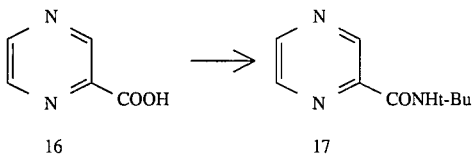

| 2-Pyrazinecarboxylic acid (8) | 3.35 kg (27 mol) |
| --- | --- |
| Oxalyl chloride | 3.46 kg (27.2 mol) |
| tert-Butylamine (KF = 460 µg/ml) | 9.36 L (89 mol) |
| EtOAc (KF = 56 µg/ml) | 27 L |
| DMF | 120 mL |
| 1-Propanol | 30 L |

The carboxylic acid 16 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5° and 8° C.

The addition was completed in 5 h. During the exothermic addition CO and $CO_2$ were evolved. The HCl that was formed remained largely in solution. A precipitate was present which is probably the HCL salt of the pyrazine acid chloride. Assay of the acid chloride formation was carried out by quenching an anhydrous sample of the reaction with t-butylamine. At completion <0.7% of acid 16 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 16=10.7 min, amide 17=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 17 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The internal temperature in this solvent change was <30° C. A 1-propanol/EtOAC solution of 3 was stable to reflux atmospheric pressure for several days.

Evaporation of an aliquot gave a tan solid m.p. 87°–88° C. $^{13}C$ NMR (75 MHz, $CDCl_3$, ppm) 161.8, 146.8, 145.0, 143.8, 142.1, 51.0, 28.5.

EXAMPLE 14 rac-2-tert-Butyl-carboxamide-piperazine 18

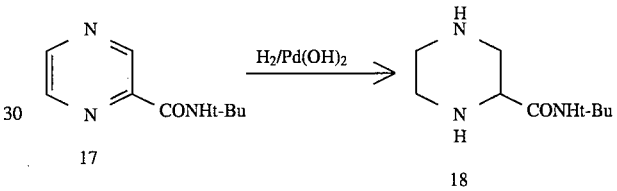

Materials
Pyrazine-2-tert-butylcarboxamide 17 2.4 kg (13.4 mol) in 1-Propanol solution 12 L 20% $Pd(OH)_2/C$ 16 wt. % water 144 g.

The pyrazine-2-tert-butylcarboxamide 17/1-propanol solution was placed into the 5 gal autoclave. The catalyst was added and the mixture was hydrogenated at 65° C. at 40 psi (3 atm) of $H_2$.

After 24 h the reaction had taken up the theoretical amount of hydrogen and GC indicated <1% of 17. The mixture was cooled, purged with N2 and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 17=7.0 min, 18=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 18 is 133 g/L.

Evaporation of an aliquot gave 18 as a white solid m.p. 150°–151° C.; $_{13}C$ NMR (75 MHz, $D_2O$, ppm) 173.5, 59.8, 52.0, 48.7, 45.0, 44.8, 28.7.

EXAMPLE 15

(S)-2-tert-Butyl-carboxamide-piperazine bis
(S)-Camphorsulfonic acid salt (S)-19

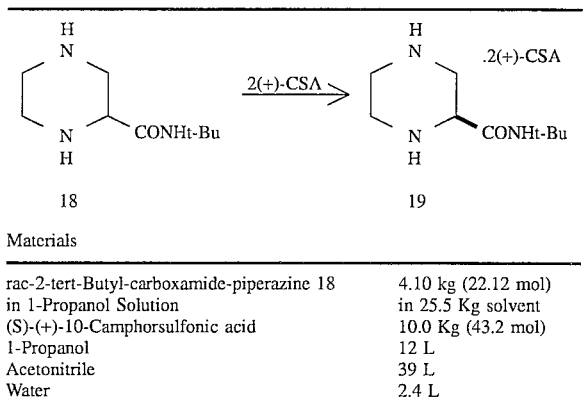

Materials

| rac-2-tert-Butyl-carboxamide-piperazine 18 in 1-Propanol Solution | 4.10 kg (22.12 mol) in 25.5 Kg solvent |
| --- | --- |
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 18 in 1-propanol was charged to a 100 L flask with an attached batch concentrator. The solution was concentrated at 10 mbar and a temperature <25° C. to a volume of ca 12 L.

At this point the product had precipitated from the solution, but went back into a solution when the mixture was heated to 50° C.

Analysis of a homogeneous aliquot indicated that the concentration of 18 was 341 g/L. The concentration was determined by HPLC: 25 cm Dupont Zorbax RXC8 column with 1.5 mL/min flow and detection at 210 nm, isocratic (98/2) $CH_3CN/0.1\%$ aqueous $H_3PO_4$. Retention time of 18:2.5 min.

Acetonitrile (39 L) and water (2.4 L) were added to give a clear, slightly brown solution.

Determination of the water content by KF titration and $CH_3CN/1$-propanol ratio by $^1H$ NMR integration showed that the $CH_3CN/1$-propanol/$H_2O$ ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21 ° C. over 8 h.

The product precipitated at 62° C. The product was filtered without aging at 21° C., and the filter cake was washed with 5 L of the $CH_3CN/1$-propanol/$H_2O$ 26/8/1.6 solvent mixture. It was dried at 35° C. in the vacuum oven with $N_2$ bleed to give 5.6 Kg (39%) of 19 as a white crystalline solid m.p. 288°–290° C. (with decomp.) $[\alpha]D^{25}=$ 18.9° (c=0.37, $H_2O$), $^{13}C$ NMR (75 MHz, $D_2O$, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 19 (33 mg) was suspended in 4 mL of EtOH and 1 mL of $Et_3N$. $Boc_2O$ (11 mg) was added and the reaction mixture was allowed to age for 1 h. The solvent was completely removed in vacuo, and the residue was dissolved in ca. 1 mL of EtOAc and filtered through a Pasteur pipet with $SiO_2$, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 16

(S)-2-tert-Butylcarboxamide-4-tert-butoxycarbonyl-piperazine 12 from salt 19

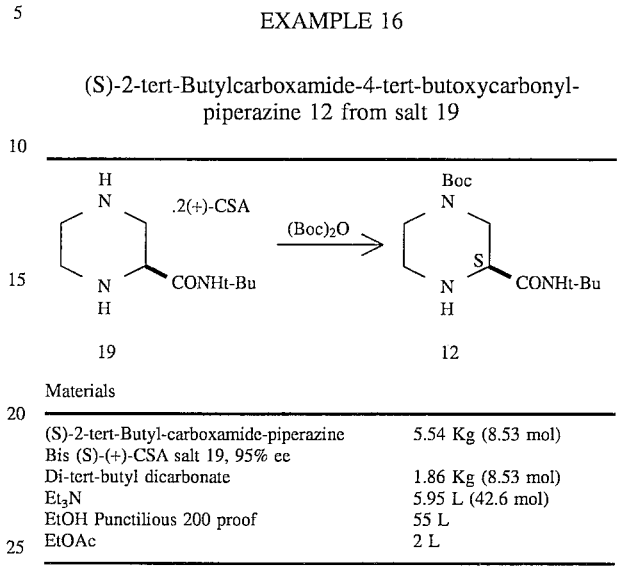

Materials

| (S)-2-tert-Butyl-carboxamide-piperazine Bis (S)-(+)-CSA salt 19, 95% ee | 5.54 Kg (8.53 mol) |
| --- | --- |
| Di-tert-butyl dicarbonate | 1.86 Kg (8.53 mol) |
| $Et_3N$ | 5.95 L (42.6 mol) |
| EtOH Punctilious 200 proof | 55 L |
| EtOAc | 2 L |

To the (S)-CSA salt 19 in a 100 L 3-neck flask with an addition funnel under $N_2$ was added EtOH, followed by triethylamine at 5° C. The solid dissolved readily on the addition of the $Et_3N$. The $Boc_2$ was dissolved in EtOAc and charged to the addition funnel. The solution of $Boc_2$ in EtOAc was added at such a rate as to keep the temperature below 25° C. The addition took 3 h. The reaction mixture was aged for 1 h after completion of the addition of the $Boc_2$O solution.

The reaction can be monitored by HPLC:25 cm Dupont Zorbax RXC8 column with 1 mL/min flow and detection at 228 nm, isocratic (50/50) $CH_3CN/0.1$ M $KH_2PO_4$ adjusted to pH=6.8 with NaOH. Retention time of 12=7.2 min. The chiral assay was carried out using the same system as in the previous step. The reaction could also be monitored by TLC with a 100% EtOAc as the solvent. (Rf=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L Di water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under $N_2$ bleed to give 1.87 Kg (77%, >99.9 area % by HPLC, R-isomer below level of detection)

of 12 as a slightly tan powder. $[\alpha]D^{25}=22.0°$ (c=0.20, MeOH), m.p. 107° C.; $_{13}$C NMR (75 MHz, CDCl$_3$, ppm) 170.1, 154.5, 79.8, 58.7, 50.6, 46.6, 43.6, 43.4, 28.6, 28.3.

EXAMPLE 17

Preparation of Racemic Indene Oxide

Indene (95%, 122 mL) was dissolved in methanol (812 mL) and acetonitrile (348 mL), then filtered. The filtrate was diluted with 0.05 M sodium dibasic phosphate (116 mL), then adjusted to pH 10.5 with 1 M aqueous sodium hydroxide. Aqueous hydrogen peroxide (35%, 105 mL) was diluted with water (53 mL) and added over 3 h, while maintaining the temperature at 25° C. and the internal pH at 10.5 with 1 M aqueous sodium hydroxide (120 mL total).

After 6 h, 1 M aqueous sodium metabisulfite was added (26 mL), while maintaining the pH above 8.3 by addition of 1 M aqueous NaOH (39 mL). Water (700 mL) was added and the mixture extracted with methylene chloride (580 mL and 300 mL). The combined organic extracts containing indene oxide (117 g) were concentrated to a volume of 600 mL.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A process of synthesizing quantitatively (1S,2S) bromo-indanol from indene, comprising the steps of
   (a) providing a mixture of one equivalent of indene, and an excess of a source of bromide ions, and haloperoxidase in buffer of pH between about 5.0 and about 8.0;
   (b) slowly mixing thereto between about one and about two equivalents of H$_2$O$_2$ and incubating the resulting second mixture until substantially all of the indene is consumed;
   (c) to give (1S,2S)-bromo-indanol.

2. A process of synthesizing quantitatively (1S,2S) bromo-indanol from indene, comprising the steps of
   (a) providing a mixture of one equivalent of indene, and haloperoxidase in buffer of pH between about 5.0 and about 8.0;
   (b) slowly mixing thereto a second mixture of an excess of a source of bromide ions and between about one and about two equivalents of H$_2$O$_2$, and incubating the resulting third mixture until substantially all of the indene is consumed;
   (c) to give (1S,2S)-bromo-indanol.

3. A process of synthesizing quantitatively (1S,2R) indanyl epoxide from indene, comprising the steps of
   (a) providing a mixture of one equivalent of indene, and an excess of a source of bromide ions, and haloperoxidase in buffer of pH between about 5.0 and about 8.0;
   (b) slowly mixing thereto between about one and about two equivalents of H$_2$O$_2$ and incubating the resulting second mixture until substantially all of the indene is consumed;
   (c) raising the pH to between about 9.0 and about 13.0;
   (d) to give (1S,2R) indanyl epoxide.

4. A process of synthesizing quantitatively (1S,2R) indanyl epoxide from indene, comprising the steps of
   (a) providing a mixture of one equivalent of indene, and haloperoxidase in buffer of pH between about 5.0 and about 8.0;
   (b) slowly mixing thereto a second mixture of an excess of a source of bromide ions and between about one and about two equivalents of H$_2$O$_2$, and incubating the resulting third mixture until substantially all of the indene is consumed;
   (c) raising the pH to between about 9.0 and about 13.0;
   (d) to give (1S,2R) indanyl epoxide.

5. A process of synthesizing quantitatively (1S,2R) indandiol from indene, comprising the steps of
   (a) providing a mixture of one equivalent of indene, and an excess of a source of bromide ions, and haloperoxidase in buffer of pH between about 5.0 and about 8.0;
   (b) slowly mixing thereto between about one and about two equivalents of H$_2$O$_2$ and incubating the resulting second mixture until substantially all of the indene is consumed;
   (c) raising the pH to between about 9.0 and about 13.0;
   (d) lowering the pH to between about 6.5 and about 3.0;
   (e) to give (1S,2R) indandiol.

6. A process of synthesizing quantitatively (1S,2R) indandiol from indene, comprising the steps of
   (a) providing a mixture of one equivalent of indene, and haloperoxidase in buffer of pH between about 5.0 and about 8.0;
   (b) slowly mixing thereto a second mixture of an excess of a source of bromide ions and between about one and about two equivalents of H$_2$O$_2$, and incubating the resulting third mixture until substantially all of the indene is consumed;
   (c) raising the pH to between about 9.0 and about 13.0;
   (d) lowering the pH to between about 6.5 and about 3.0;
   (e) to give (1S,2R) indandiol.

7. The process according to any of claims 1–6, wherein the buffer is a phosphate buffer with a pH between about 6.5 and about 7.5.

8. The process according to any of claims 1–6, wherein the haloperoxidase is a suspension of fungal cells containing the enzyme haloperoxidase.

9. The process according to any of claims 1–6, wherein the haloperoxidase is a supernatant of fungal cell culture containing the enzyme haloperoxidase.

10. The process according to any of claims 1–6, wherein the haloperoxidase is the re-suspension after ammonium salt precipitation of fungal cell culture supernatant, said supernatant containing the enzyme haloperoxidase.

11. The process of claim 10 wherein the fungal cells are *Curvularia protuberata* MF 5400, or are derived from ATCC 74332.

12. The process according to any of claims 1–6, wherein the source of bromide ions is NaBr or KBr or mixture thereof.

13. A process of synthesizing quantitatively (1S,2S) bromo-indanol from indene, comprising the steps of
   (a) providing a mixture of one equivalent of indene and an excess of KBr, and *Curvularia protuberata* MF 5400 haloperoxidase in phosphate buffer of pH of about 7.0;
   (b) slowly mixing thereto between about one and about two equivalents of H$_2$O$_2$ and incubating the resulting second mixture until substantially all of the indene is consumed;
   (c) to give (1S,2S)-bromo-indanol.

14. A process of synthesizing quantitatively (1S,2S) bromo-indanol from indene, comprising the steps of
   (a) providing a mixture of one equivalent of indene, and *Curvularia protuberata* MF 5400 haloperoxidase in phosphate buffer of pH of about 7.0;
   (b) slowly mixing thereto a second mixture of an excess of KBr and between about one and about two equivalents of $H_2O_2$, and incubating the resulting third mixture until substantially all of the indene is consumed;
   (c) to give (1S,2S)-bromo-indanol.

15. A process of synthesizing quantitatively (1S,2R) indanyl epoxide from indene, comprising the steps of
   (a) providing a mixture of one equivalent of indene and an excess of KBr, and *Curvularia protuberata* MF 5400 haloperoxidase in phosphate buffer of pH of about 7.0;
   (b) slowly mixing thereto between about one and about two equivalents of $H_2O_2$ and incubating the resulting second mixture until substantially all of the indene is consumed;
   (c) raising the pH to about 12.5;
   (d) to give (1S,2R) indanyl epoxide.

16. A process of synthesizing quantitatively (1S,2R) indanyl epoxide from indene, comprising the steps of
   (a) providing a mixture of one equivalent of indene, and *Curvularia protuberata* MF 5400 haloperoxidase in phosphate buffer of pH of about 7.0;
   (b) slowly mixing thereto a second mixture of an excess of KBr and between about one and about two equivalents of $H_2O_2$, and incubating the resulting third mixture until substantially all of the indene is consumed;
   (c) raising the pH to about 12.5;
   (d) to give (1S,2R) indanyl epoxide.

17. A process of synthesizing quantitatively (1S,2R) indandiol from indene, comprising the steps of
   (a) providing a mixture of one equivalent of indene, and an excess of KBr, and *Curvularia protuberata* MF 5400 haloperoxidase in phosphate buffer of pH of about 7.0;
   (b) slowly mixing thereto between about one and about two equivalents of $H_2O_2$ and incubating the resulting second mixture until substantially all of the indene is consumed;
   (c) raising the pH to about 12.5;
   (d) lowering the pH to about 5.0;
   (e) to give (1S,2R) indandiol.

18. A process of synthesizing quantitatively (1S,2R) indandiol from indene, comprising the steps of
   (a) providing a mixture of one equivalent of indene, and *Curvularia protuberata* MF 5400 haloperoxidase in phosphate buffer of pH of about 7.0;
   (b) slowly mixing thereto a second mixture of an excess of KBr, and between about one and about two equivalents of $H_2O_2$, and incubating the resulting third mixture until substantially all of the indene is consumed;
   (c) raising the pH to about 12.5;
   (d) lowering the pH to about 5.0;
   (e) to give (1S,2R) indandiol.

* * * * *